(12) United States Patent
Prewitt

(10) Patent No.: US 9,358,084 B2
(45) Date of Patent: Jun. 7, 2016

(54) ORTHODONTIC RETAINER CLEANING CASE

(75) Inventor: Mary Julia Prewitt, Fayetteville, NC (US)

(73) Assignee: Julia Prewitt, Wrightsville Beach, NC (US)

(*) Notice: Subject to any disclaimer, the term of this patent is extended or adjusted under 35 U.S.C. 154(b) by 1033 days.

(21) Appl. No.: 13/006,770

(22) Filed: Jan. 14, 2011

(65) Prior Publication Data

US 2012/0181192 A1 Jul. 19, 2012

(51) Int. Cl.
*A61C 17/00* (2006.01)
*A45D 44/20* (2006.01)
*A47L 25/00* (2006.01)
*A61L 2/00* (2006.01)
*A61C 7/08* (2006.01)

(52) U.S. Cl.
CPC .............. *A61C 17/036* (2013.01); *A45D 44/20* (2013.01); *A47L 25/00* (2013.01); *A61C 7/08* (2013.01); *A61L 2/0088* (2013.01)

(58) Field of Classification Search
CPC ...... A61C 7/008; A61C 17/036; A61C 15/00; A61C 19/002; A61C 19/008; A47L 25/00; B08B 3/08; B08B 11/02; A45D 44/20; A61L 2/0088; A61L 2/18; A61L 2202/17
USPC ............... 206/368.5, 63.5; 128/859; 134/137, 134/155; 422/301; D3/294; D24/227; D28/73; 15/97
See application file for complete search history.

(56) References Cited

U.S. PATENT DOCUMENTS

| 1,345,123 | A | * | 6/1920 | Bryant | 422/301 |
|---|---|---|---|---|---|
| 1,365,686 | A | * | 1/1921 | Harvey | 422/300 |
| 1,676,090 | A | * | 7/1928 | Johnson | 422/301 |
| 1,683,458 | A | * | 9/1928 | Garrison | A61C 17/02 15/21.1 |
| 2,163,862 | A | * | 6/1939 | Wing | 134/137 |
| 3,130,860 | A | * | 4/1964 | Oberkircher | 206/509 |
| 3,149,358 | A | * | 9/1964 | Chadbourne | 15/21.1 |
| 3,904,058 | A | * | 9/1975 | Rosenstein | A61C 17/036 134/117 |
| 5,000,209 | A | * | 3/1991 | Mann | 134/135 |
| 5,314,543 | A | * | 5/1994 | Elkins et al. | 134/1 |
| 6,213,777 | B1 | * | 4/2001 | Seitzinger | 433/229 |
| 6,390,104 | B1 | * | 5/2002 | Gagnon | 134/107 |
| 7,041,261 | B2 | * | 5/2006 | Margolis | 422/301 |
| 7,798,159 | B2 | * | 9/2010 | Palfy et al. | 134/184 |
| 8,353,305 | B1 | * | 1/2013 | Barham | 134/93 |
| 2006/0157089 | A1 | * | 7/2006 | Taylor et al. | 134/52 |
| 2007/0142254 | A1 | * | 6/2007 | Arce | A45C 11/00 510/117 |
| 2008/0283422 | A1 | * | 11/2008 | Jansheski | B65D 43/164 206/63.5 |
| 2010/0186780 | A1 | * | 7/2010 | Larocca et al. | 134/105 |
| 2010/0330535 | A1 | * | 12/2010 | Adusimilli et al. | 433/199.1 |

FOREIGN PATENT DOCUMENTS

| CN | 2744173 Y | * | 12/2005 | |
|---|---|---|---|---|
| CN | 201398892 Y | * | 2/2010 | |
| DE | 3511305 A1 | * | 10/1986 | A45D 44/20 |
| EP | 766969 A1 | * | 4/1997 | |
| JP | 62155044 A | * | 7/1987 | |
| JP | 09289921 A | * | 11/1997 | |
| TW | EP 1110477 A1 | * | 6/2001 | A45D 44/20 |

OTHER PUBLICATIONS

My Retainer Classic Case, myretainer.com, dated Oct. 2008 (available at https://web.archive.org/web/20081006000742/http://www.myretainer.com/ClassicCase.htm) ("MyRetainer").*
eGullet, Japanese Kitchen Gadgets & Equipment, Pickle Press at p. 3, dated Dec. 2004 (available at http://forums.egullet.org/topic/58044-japanese-kitchen-gadgets-equipment/page-2).*
Machine translation of DE 3511305 A1, dated Oct. 1986.*
Machine translation of CN 201398892 Y, dated Feb. 2010.*

* cited by examiner

*Primary Examiner* — Joseph L Perrin
*Assistant Examiner* — Kevin G Lee
(74) *Attorney, Agent, or Firm* — Triangle Patents, PLLC

(57) ABSTRACT

A lidded plastic container has a plunger in the lid which pushes clear trays (that usually float) down into a cleaning solution. The container may include vent holes in its lid to allow gas evolving cleaning agents to vent without building up pressure inside the container.

13 Claims, 2 Drawing Sheets

ORTHODONTIC RETAINER CLEANING CASE

BACKGROUND OF THE INVENTION

The present invention relates to an orthodontic retainer cleaning case and, more particularly, to an orthodontic retainer cleaning case having a plunger to submerge retainers in the solution.

Conventional retainer cleaning tablet instructions inform the user to place the retainer in a glass of water, similar to denture cleaning instructions. However, dentures sink in water but clear plastic retainers and INVISALIGN® trays float, resulting in difficulties in surrounding the retainer/INVISALIGN® tray with water/cleaning solution.

As can be seen, there is a need for an apparatus for cleaning orthodontic appliances that prevents orthodontic retainers/INVISALIGN® trays from floating in their cleaning case during cleaning.

SUMMARY OF THE INVENTION

In one aspect of the present invention, a cleaning container for holding a substrate under the surface of a liquid, comprises of a base adapted to hold the liquid; a lid adapted to close against the base; a plunger attached to the lid, the plunger adapted to hold the substrate below the surface of the liquid when the substrate and the liquid are present in the base.

In another aspect of the present invention, a cleaning container comprises a base adapted to hold a cleaning solution; a lid adapted to fit on the base; at least one slot cut through the lid; a disc-shaped plunger descending from an underside of the lid, wherein the plunger is disposed below a surface of the cleaning solution when the cleaning solution is in the cleaning container, wherein the plunger is adapted to hold a retainer below the surface of the cleaning solution when the retainer and the cleaning solution are present in the base.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, an embodiment of the present invention provides a lidded plastic container that has a plunger in the lid which pushes clear trays (that usually float) down into a cleaning solution. The container may include vent holes in its lid to allow gas evolving cleaning agents to vent without building up pressure inside the container.

Figure 1:
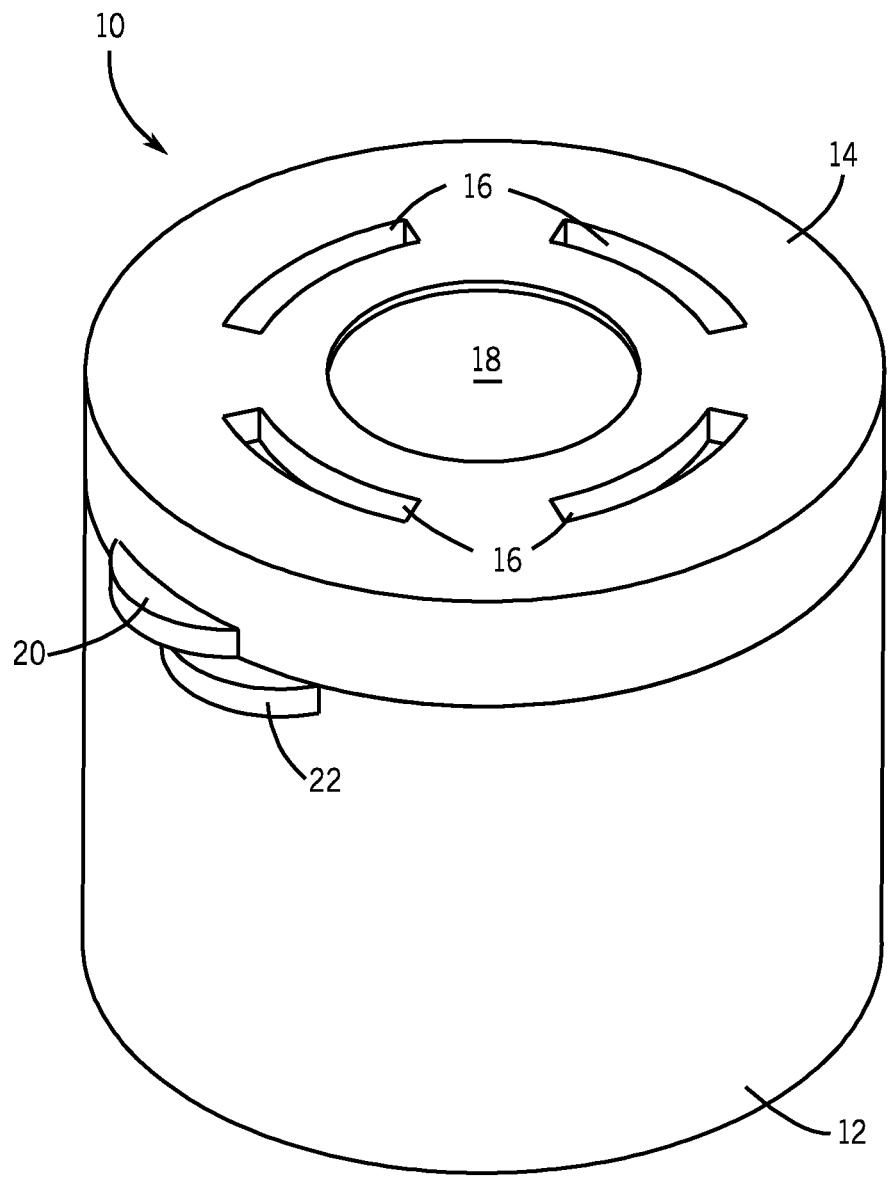
FIG. 1 is a perspective view of a cleaning case according to an exemplary embodiment of the present invention.
Figure 2:
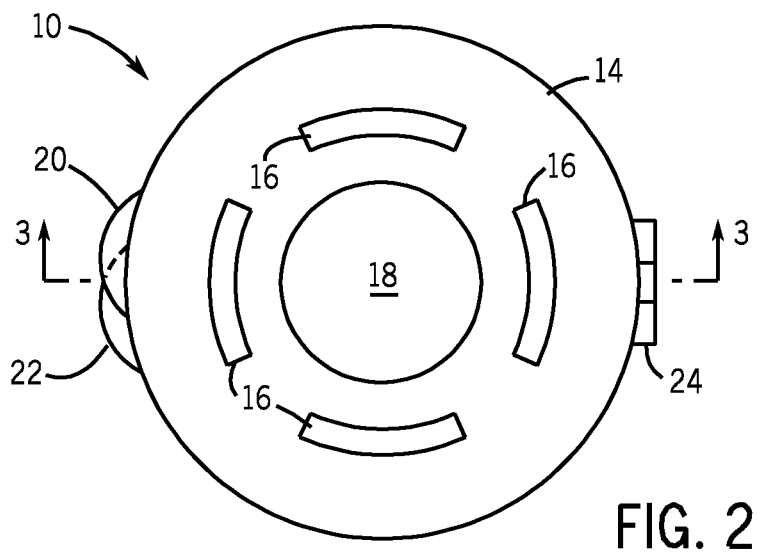
FIG. 2 is a top view of the cleaning case of FIG. 1.
Figure 3:
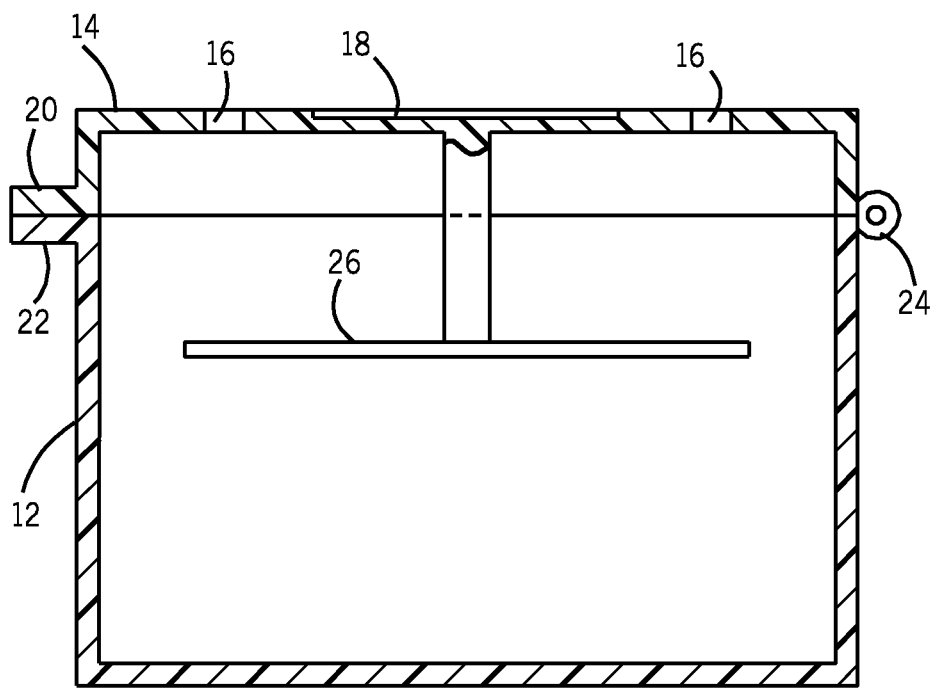
FIG. 3 is a cross-sectional view of the cleaning case of FIG. 1 taken along line 3-3 of FIG. 2.

Referring to FIGS. 1 through 3, a cleaning container 10 may include a base 12 and a lid 14. The lid 14 may be hingeably attached to the base 12 with a hinge 24. The hinge 24 may be of any conventional design, such as a hole and pin design or a living hinge type of design.

The cleaning container 10 may, for example, be about 3-5 inches in diameter, typically about 4 inches in diameter, and about 2-4 inches in height, typically about 3 inches in height. In some embodiments, the lid 14 may be about ½ inch in height, while the base 12 may be about 2.75 inches high. The lid 14 may include one or more vent holes 16. In one embodiment, the vent holes 16 may be disposed as slits in the top surface of the lid 14. The vent holes 16 may permit cleaning products that evolve gas to vent without pressure building up in the cleaning container 10.

A recess 18 may be provided in the lid 14. The recess 18 may be used to apply a logo, insignia or the like. The recess 18 may be disposed in a central region on the top surface of the lid 14.

A plunger 26 may extend from an underside of the lid 14. The plunger 26 may be from about 2 to about 4 inches in diameter, typically about 3 inches in diameter. In some embodiments, the plunger 26 is from 0.5 to 1.5 inches smaller in diameter than the diameter of the base 12. The plunger 26 may be disposed from about 1 to about 2 inches below the lid, typically about 1.25 inches below the lid to allow the plunger 26 to hold a substrate to be cleaned (such as a retainer tray, a retainer, an INVISALIGN® tray, or the like, to be held below the surface of cleaning solution disposed in the base 12 of the cleaning container 10. The plunger 26 may be a flat piece of material, such as plastic, or may be slotted, contoured, or the like, to permit the plunger to hold a retainer under cleaning solution disposed in the container 10.

The lid 14 may seal against the base 12 when the lid 14 is closed against the base 12. In some embodiments, the lid 14 may include a protrusion and the base 12 may include an inset adapted to receive the protrusion when the lid 14 is closed on the base 12. The protrusion and inset may be, for example, about 2 mm thick and may frictionally fit together. In other embodiments, a sealing member (not shown), such as an o-ring, may be disposed between the lid 14 and the base 12. In still other embodiments, the lid 14 may sit flat against the base 12.

The lid 14 and the base 12 may include one or more tabs 20, 22 to aid in opening and closing the container 10. The tabs 20, 22 may be offset to provide a leverage point for opening the lid 14 from the base 12. In some embodiments, the tabs 20, 22 may include a mechanism to help keep the container 10 closed. For example, the one tab may include a protrusion, while the other may include a socket, where the protrusion fits into the socket when the container 10 is closed. Other configurations of the tabs 20, 22 may be within the scope of the present invention.

The container 10 may include optional elements, such as a brush holder (not shown) for holding a retainer cleaning brush. This may be useful to keep the retainer cleaning brush close at hand for use before and/or after soaking the retainer in cleaning solution disposed in the container 10.

A user may place their retainer in the base 12 of the container 10 and fill the base 12 with about 2 inches of cleaning liquid (also, a cleaning tablet could be added to the liquid, such as water). The lid 14 could then be closed, which would allow the plunger 26 to push the retainer into the liquid. Once the cleaner has been given the desired working time, the lid 14 may be opened and the retainer may float to the surface of the liquid. The retainer can then be removed and the liquid poured out. The container 10 may be cleaned and the lid 14 closed on the base 12 for storage.

It should be understood, of course, that the foregoing relates to exemplary embodiments of the invention and that modifications may be made without departing from the spirit and scope of the invention as set forth in the following claims.

What is claimed is:

1. A cleaning container for holding a retainer or a retainer tray which floats in a liquid under the surface of the liquid, the cleaning container consisting essentially of:
    a base adapted to hold the liquid and at least having a bottom;
    a lid adapted to close against the base and at least having a top and at least four vent holes;
    a hinge connecting the lid and the base for hinged opening and closing of the lid;
    a plunger attached to the underside of the lid and including a protrusion stem located approximately in the center of the underside of the lid and a disc, wherein the disc is slotted to facilitate downward and upward movement of the disc through the liquid and wherein the disc is flat;
    the protrusion stem immovably affixed perpendicularly to the lid at one end and immovably affixed perpendicularly to the disc at the other end;
    the disc adapted to directly hold the retainer or the retainer tray below the surface of the liquid by physically contacting the retainer or the retainer tray from above, wherein the retainer or the retainer tray is not supported by any part of the container from underneath when the retainer or the retainer tray and the liquid are present in the base;
    wherein the lid includes a protrusion and wherein the base includes an inset operable to receive the protrusion when the lid is closed against the base;
    wherein the base further includes an o-ring, wherein the o-ring provides a seal between the base and the lid when the lid is closed against the base;
    wherein the lid includes a recess in the central region on the top surface of the lid;
    wherein the cleaning container includes at least one lid tab disposed on the lid and at least one base tab disposed on the base;
    wherein when the lid is closed against the base, the disc is positioned approximately one-third of the distance from the top of the lid to the bottom of the base to submerge the retainer or the retainer tray under the surface of the liquid and allow the hinge to close when the lid is closed against the base, wherein the disc does not contact the container during the closure of the lid;
    wherein the disc does not include spacers for holding the retainer or the retainer tray in place under the liquid;
    wherein the at least four vent holes allow gases produced from the interaction of the liquid and the retainer or the retainer tray to vent without building up pressure inside the container;
    wherein the protrusion, the inset, and the o-ring are operable to ensure the lid remains closed against the base during cleaning of the retainer or the retainer tray and the protrusion is inserted in the inset and to ensure that the gases produced from the interaction of the liquid and the retainer or the retainer tray vent through the at least four vent holes instead of through another part of the container;
    wherein the disc does not include an integrated brush;
    wherein the cleaning container does not include a motor; and
    wherein the cleaning container, including the base, the lid, the hinge, and the plunger, is formed of a unitary plastic material.

2. The cleaning container of claim 1, wherein the hinge is positioned away from the lid top approximately one-fifth of the distance between the lid top and base bottom when the container is closed.

3. The cleaning container of claim 2, wherein the plunger's diameter is between 2 inches and 4 inches and the plunger's length is between 1 inch and 2 inches.

4. The cleaning container of claim 2, wherein the container's diameter is between 3 inches and 5 inches, the container's height is between 2 inches and 4 inches, the lid has a height of ½ inch, the base has a height of 2.75 inches, the plunger diameter is between 2 inches and 4 inches and plunger length is between 1 inch and 2 inches.

5. The cleaning container of claim 1, wherein the height of the container is between 2 inches and 4 inches, the height of the lid is ½ inches, and the height of the base is 2.75 inches.

6. The cleaning container of claim 1, wherein the tabs are offset from each other when the lid is closed against the base.

7. A cleaning container for holding a retainer or a retainer tray which floats in a cleaning solution under the surface of the cleaning solution comprising:
    a base adapted to hold the cleaning solution and at least having a bottom;
    a lid adapted to fit on the base and at least having a top and at least four vent holes cut through the lid; wherein the lid further includes a top flat member and a downwardly dependent side member;
    a hinge positioned to connect the lid and the base at the downwardly depending side member of the lid;
    a disc-shaped plunger descending from an underside of the lid and comprising a protrusion stem and a disc, wherein the disc is flat;
    the protrusion stem perpendicularly, immovably affixed to the approximate center of the lid at one end and perpendicularly, immovably affixed to the disc at the other end;
    wherein the disc is disposed below a surface of the cleaning solution when the cleaning solution is used in the cleaning container;
    wherein the disc is adapted to directly hold the retainer or the retainer tray below the surface of the cleaning solution by physically contacting the retainer or the retainer tray from above, wherein the retainer or the retainer tray is not supported by any part of the container from underneath when the retainer or the retainer tray and the cleaning solution are present in the base;
    wherein the lid includes a protrusion and wherein the base includes an inset operable to receive the protrusion when the lid is closed against the base;
    wherein the base further includes an o-ring, wherein the o-ring provides a seal between the base and the lid when the lid is closed against the base;
    wherein the lid includes a recess in the central region on the top surface of the lid;
    wherein the cleaning container includes at least one lid tab disposed on the lid and at least one base tab disposed on the base;
    wherein when the lid is closed against the base, the disc is positioned approximately one-third of the distance from the top of the lid to the bottom of the base to submerge the retainer or the retainer tray under the surface of the cleaning solution and allow the hinge to close when the lid is closed against the base, wherein the disc does not contact the container during the closure of the lid;

wherein the disc does not include spacers for holding the retainer or the retainer tray in place under the cleaning solution;

wherein the at least four vent holes allows gases produced from the interaction of the cleaning solution and the retainer or the retainer tray to vent without building up pressure inside the container;

wherein the protrusion, the inset, and the o-ring are operable to ensure the lid remains closed against the base during cleaning of the retainer or the retainer tray to ensure that the gases produced from the interaction of the cleaning solution and the retainer or the retainer tray vent through the at least four vent holes instead of through another part of the container;

wherein the disc does not include an integrated brush;

wherein the cleaning container does not include a motor; and wherein the cleaning container, including the base, the lid, the hinge, and the plunger, is formed of a unitary plastic material.

8. The cleaning container of claim 7, wherein the tabs are offset from each other and provide a leverage point for opening the lid from the base using the at least one lid tab when the lid is closed against the base.

9. The cleaning container of claim 7, where the hinge is positioned away from the lid top approximately one-fifth of the distance between the lid top and base bottom when the container is closed.

10. The cleaning container of claim 7, where the plunger has a diameter less than a diameter of the base.

11. A cleaning container for holding a retainer, a retainer tray, or an INVISALIGN tray which floats in a cleaning solution under the surface of the cleaning solution comprising:

a base adapted to hold the cleaning solution and at least having a bottom;

a lid adapted to fit on the base and at least having a top and at least four vent holes cut through the lid; wherein the lid further includes a top flat member and a downwardly dependent side member;

a hinge positioned to connect the lid and the base at the downwardly depending side member of the lid; wherein the hinge is positioned away from the lid top one-fifth of the distance between the lid top and base bottom when the container is closed;

a disc-shaped plunger descending from an underside of the lid and comprising a protrusion stem and a disc, wherein the disc is flat;

the protrusion stem perpendicularly, immovably affixed to the approximate center of the lid at one end and perpendicularly, immovably affixed to the disc at the other end;

wherein the disc is disposed below a surface of the cleaning solution when the cleaning solution is used in the cleaning container;

wherein the disc is adapted to directly hold the retainer, the retainer tray, or the INVISALIGN tray below the surface of the cleaning solution by physically contacting the retainer, the retainer tray, or the INVISALIGN tray from above, wherein the retainer, the retainer tray, or the INVISALIGN tray is not supported by any part of the container from underneath when the retainer, the retainer tray, or the INVISALIGN tray and the cleaning solution are present in the base;

wherein the lid includes a protrusion and wherein the base includes an inset operable to receive the protrusion when the lid is closed against the base;

wherein the base further includes an o-ring, wherein the o-ring provides a seal between the base and the lid when the lid is closed against the base;

wherein the lid includes a recess in the central region on the top surface of the lid;

wherein the cleaning container includes at least one lid tab disposed on the lid and at least one base tab disposed on the base;

wherein when the lid is closed against the base, the disc is positioned approximately one-third of the distance from the top of the lid to the bottom of the base to submerge the retainer, the retainer tray, or the INVISALIGN tray under the surface of the cleaning solution and allow the hinge to close when the lid is closed against the base, wherein the disc does not contact the container during the closure of the lid;

wherein the disc does not include spacers for holding the retainer, the retainer tray, or the INVISALIGN tray in place under the cleaning solution;

wherein the at least four vent holes allow gases produced from the interaction of the cleaning solution and the retainer, the retainer tray, or the INVISALIGN tray to vent without building up pressure inside the container;

wherein the protrusion, the inset, and the o-ring are operable to ensure the lid remains closed against the base during cleaning of the retainer, the retainer tray, or the INVISALIGN tray and to ensure that the gases produced from the interaction of the cleaning solution and the retainer, the retainer tray, or the INVISALIGN tray vent through the at least four vent holes instead of through another part of the container;

wherein the disc does not include an integrated brush;

wherein the cleaning container does not include a motor; and wherein the cleaning container, including the base, the lid, the hinge, and the plunger, is formed of a unitary plastic material.

12. The cleaning container of claim 11, wherein the container's diameter is between 3 inches and 5 inches, the container's height is between 2 inches and 4 inches, the lid has a height of ½ inch, the base has a height of 2.75 inches, the plunger diameter is between 2 inches and 4 inches and plunger length is between 1 inch and 2 inches.

13. A system for cleaning a retainer or a retainer tray which floats in a cleaning solution under the surface of the cleaning solution, the system comprising the retainer or the retainer tray which floats in the cleaning solution, the cleaning solution, and a cleaning container for holding the retainer or the retainer tray which floats in the cleaning solution under the surface of the cleaning solution, the cleaning container including:

a base adapted to hold the cleaning solution and at least having a bottom;

a lid adapted to close against the base and at least having a top and at least four vent holes;

a hinge connecting the lid and the base for hinged opening and closing of the lid;

a plunger attached to the underside of the lid and comprising a protrusion stem located approximately in the center of the underside of the lid and a disc, wherein the disc is slotted to facilitate downward and upward movement of the disc through the cleaning solution and wherein the disc is flat;

the protrusion stem immovably affixed perpendicularly to the lid at one end and immovably affixed perpendicularly to the disc at the other end;

the disc adapted to directly hold the retainer or the retainer tray below the surface of the cleaning solution by physically contacting the retainer or the retainer tray from above, wherein the retainer or the retainer tray is not supported by any part of the container from underneath when the retainer or the retainer tray and the cleaning solution are present in the base;

wherein the lid includes a protrusion and wherein the base includes an inset operable to receive the protrusion when the lid is closed against the base;

wherein the base further includes an o-ring, wherein the o-ring provides a seal between the base and the lid when the lid is closed against the base;

wherein the lid includes a recess in the central region on the top surface of the lid;

wherein the cleaning container includes at least one lid tab disposed on the lid and at least one base tab disposed on the base;

wherein when the lid is closed against the base, the disc is positioned approximately one-third of the distance from the top of the lid to the bottom of the base to submerge the retainer or the retainer tray under the surface of the cleaning solution and allow the hinge to close when the lid is closed against the base, wherein the disc does not contact the container during the closure of the lid;

wherein the disc does not include spacers for holding the retainer or the retainer tray in place under the cleaning solution;

wherein the at least four vent holes allow gases produced from the interaction of the cleaning solution and the retainer or the retainer tray to vent without building up pressure inside the container;

wherein the protrusion, the inset, and the o-ring are operable to ensure the lid remains closed against the base during cleaning of the retainer or the retainer tray and to ensure that the gases produced from the interaction of the cleaning solution and the retainer or the retainer tray vent through the at least four vent holes instead of through another part of the container;

wherein the disc does not include an integrated brush;

wherein the cleaning container does not include a motor; and wherein the cleaning container, including the base, the lid, the hinge, and the plunger, is formed of a unitary plastic material.

\* \* \* \* \*